United States Patent [19]

Okazaki et al.

[11] 4,260,599

[45] Apr. 7, 1981

[54] ANTIFIBROTIC SUBSTANCE P-1894B

[75] Inventors: Hisayoshi Okazaki, Kyoto; Tsuneo Kanamaru, Takatsuki; Kazuhiko Ohta, Ikeda, all of Japan

[73] Assignee: Takeda Chemical Industries, Ltd., Japan

[21] Appl. No.: 60,863

[22] Filed: Jul. 26, 1979

[30] Foreign Application Priority Data

Aug. 7, 1978 [JP] Japan ................... 53/96553

[51] Int. Cl.$^3$ ............................................. A61K 35/00
[52] U.S. Cl. .................................................. 424/122
[58] Field of Search ....................... 424/122; 435/169

Primary Examiner—Jerome D. Goldberg
Attorney, Agent, or Firm—Wenderoth, Lind & Ponack

[57] ABSTRACT

An antifibrotic substance P-1894B is produced by cultivating a microorganism belonging to the genus Streptomyces and being capable of producing P-1894B in a culture medium to have Antifibrotic substance P-1894B elaborated and accumulated in the cultured broth and recovering the substance.

P-1894B is effective for the prophylaxis or treatment of the fibrosis due to excessive collagen accumulation in mammal.

6 Claims, 3 Drawing Figures

ANTIFIBROTIC SUBSTANCE P-1894B

This invention relates to an antifibrotic substance P-1894B which has protocollagen proline hydroxylase inhibitor activity, collagen biosynthesis inhibitor activity and other properties.

Protocollagen proline hydroxylase is an enzyme which specifically hydroxylates the proline residue of the protocollagen synthesized by ribosome in animal cells and is one of the important rate-limiting factors in the biosynthesis of collagen. As inhibitors of this enzymic activity, there are known iron chelators (e.g. $\alpha$, $\alpha'$-dipyridyl, etc.), SH enzyme inhibitors (e.g. p-chloromercury benzoate, etc.), certain heavy metals (e.g. $Cu^{++}$, $Zn^{++}$, etc.) and so forth. These substances, however, caused serious side effects in animals and could not be used as drugs, for they invariably inhibit both the biosynthesis of collagen and that of non-collagenous proteins non-specifically. It was evident that if a substance be discovered which would not inhibit biosynthesis of non-collagenous protein but would specifically inhibit collagen biosynthesis alone, it could be successfully utilized for the prophylaxis and treatment of diseases including various forms of organ fibrosis accompanied by an excess accumulation of collagen, such as arteriosclerosis, hepatic cirrhosis, keloid, scleroderma, rheumatic arthritis, pulmonary fibrosis, etc.

We investigated many microbial metabolites for inhibitors of protocollagen proline hydroxylase and discovered an antifibrotic substance P-1894B which specifically inhibited collagen biosynthesis (The substance will hereinafter be referred to sometimes briefly as P-1894B). This invention has been conceived and developed on the basis of the above finding.

Thus, an object of this invention is to provide a new antifibrotic substance P-1894B.

Another object of this invention is to provide a process for producing an antifibrotic substance P-1894B, which comprises culturing a P-1894B-producing microorganism belonging to the genus Streptomyces in a culture medium containing an assimilable carbon source and a digestible nitrogen source under aerobic conditions until the P-1894B has accumulated in the culture medium, and recovering the P-1894B therefrom and still another object is to provide a composition for inhibiting animal tissue fibrosis which contains an antifibrotic substance P-1894B. Further objects will become clear in the following description and claims.

This invention may be carried into practice with the aid of any desired strain of microorganism only if such strain belongs to the genus Streptomyces and is able to elaborate an antifibrotic substance P-1894B. In this specification, such a strain or strains of microorganism will sometimes be referred to as the P-1894B-producer or producers. As the most desirable and representative P-1894B-producers, there may be mentioned Streptomyces sp. No. 1894 and Streptomyces sp. No. 1953, both of which have been isolated from soil samples. These two strains have later been identified as Streptomyces albogriseolus subsp. No. 1894 and Streptomyces albogriseolus No. 1953, respectively. Of these strains, Streptomyces albogriseolus subsp. No. 1894 has been deposited at the Institute for Fermentation under the accession number of IFO 13881, at the Agency of Industrial Science and Technology, Fermentation Research Institute under the deposit number of FERM-P No. 4575 and at the American Type Culture Collection under the identification number of ATCC 31422. Streptomyces albogriseolus No. 1953 have also been deposited at the same institutions under the numbers of IFO 13882, FERM-P No. 4576 and ATCC 31423, respectively.

The characteristics of the above-mentioned two strains of microorganisms as examined by procedures similar to those described in International Journal of Systematic Bacteriology 16, 3, p.p.313–340 (1966) are as follows. Unless otherwise indicated, the cultural characteristics are those observed by cultivating each strain at 28° C. for 14 days.

(1) Streptomyces albogriseolus subsp. No. 1894

(I) Morphological characteristics

The spore-bearing hyphae were simply branched from vegetative mycelia and spores occured in chains of more than 10. The form of spore-bearing aerial hyphae was spiral, open loops, flexibilis and occasionally hook. Whorls were not observed. Spores were ellipsoidal to cylindrical, 0.4 to 0.6×0.7 to 1.2µ. The surface of spores were warty [sucrose-nitrate agar, starch-inorganic salt agar (ISP-4)], sometimes short stant spiny [tyrosine agar (ISP-7), yeast-malt agar (ISP-2)] and/or smooth [glycerin-asparagine agar (ISP-5)].

(II) Cultural characteristics

The degrees of growth, colors of aerial mycelia, reverse colors, colors of soluble pigments, if produced, and other cultural features on various media are presented in Table 1. The standard color code shown in parentheses in connection with each description of color has been taken from the Color Harmony Manual of Container Corporation of America.

TABLE 1

Cultural characteristics of Streptomyces albagriseolus subsp. No. 1894 on various media

| Medium | Growth | Aerial mycelium | Reverse side of substrate mycelium | Soluble pigments |
|---|---|---|---|---|
| Sucrose-nitrate agar | Moderate, colorless to light ivory (2ca) | Moderate, powdery, gray (near grays, 2cb, ivory tint, partially 2dc natural string) | Colorless to light yellowish gray | None |
| Glucose-asparagine agar | Moderate, gray( near grays, 3cb, sand) to light wheat (2ea) | Poor to moderate, white to gray (2cb) | Gray to collonial yellow (2ga), bamboo (2gc) | None |
| Glycerine-asparagine agar (ISP-medium 5) | Moderate, light wheat (2ea) | Abundant, powdery, white, ivory to gray (near grays, 2cb, partially 2dc) | Light tan (3gc) to light amber (3ic) | Pale brown |
| Inorganic salts- | Moderate, raised, | Moderate, powdery, | Light wheat to | |

TABLE 1-continued

Cultural characteristics of *Streptomyces albagriseolus* subsp. No. 1894 on various media

| Medium | Growth | Aerial mycelium | Reverse side of substrate mycelium | Soluble pigments |
|---|---|---|---|---|
| starch agar (ISP-medium 4) | light wheat (2ea) | white to gray (near grays 2cb to 2dc) | mustard (2ea, 2gc, 21e) | None |
| Tyrosine agar (ISP-medium 7) | Moderate, gray ( near grays, 3cb) | Moderate, powdery, gray (near grays, 2dc, partially 1fe) | Gray to dark gray with pale yellowish brown | None |
| Nutrient agar | Moderate, colorless to light ivory (2ca) | Poor, white | Colorless to ivory | None |
| Yeast-malt agar (ISP-medium 2) | Abundant, wrinkled or holded, colorless to light wheat | Moderate, powdery, ivory (2ca to 2ea) to gray (near grays, 2cb) | Amber (3pc) to golden brown (3pg) | Pale-yellowish brown |
| Oatmeal agar (ISP-medium 3) | Moderate, colorless to light wheat (2ea) | Poor, powdery, white | Colorless to light wheat | Pale yellowish brown |

(III) Physiological characteristics (a) Temperature range for growth:

Growth on maltose yeast extract agar (1% maltose, 0.4% yeast extract and 2% agar, pH 7.0) was observed for a period of 2 weeks. As shown in Table 2, the optimum temperature range for growth of this strain was 28°–40° C.

TABLE 2

| Growth temperature (°C.) | Degree of growth | Growth temperature (°C.) | Degree of growth |
|---|---|---|---|
| 15 | + | 32 | +++ |
| 20 | ++ | 37 | +++ |
| 24 | ++ | 40 | +++ |
| 28 | +++ | 45 | ++ |
| 30 | +++ | 55 | − |

(Note) In the table,
−: no growth,
+: growth,
++: good growth,
+++: luxuriant growth.

(b) Liquefaction of gelatin (glucose-peptone gelatin, 28° C., 3 weeks): positive but very weak;

(c) Hydrolysis of starch (starch-inorganic salt agar, 28° C.): positive;

(d) Coagulation and peptonization of skim milk (skim milk, 37° C.); positive coagulation and positive but weak peptonization;

(e) Reduction of nitrates (peptone water with 1% potassium nitrate, 28° C., 3 weeks): negative;

(f) Production of melanoid pigments:

No melanoid pigment production in any of tyrosine agar, peptone-yeast extract-iron agar (ISP 6) and tryptone-yeast broth (ISP 1);

(IV) Assimilation of carbon sources (Pridham-Gotlieb agar (ISP 9), 28° C.):

The carbohydrate assimilation spectrum of this strain is presented in Table 3.

TABLE 3

| Carbon source | Degree of assimilation | Carbon source | Degree of assimilation |
|---|---|---|---|
| L-Arabinose | ++ | i-Inositol | ± |
| D-Xylose | + | L-Rhamnose | ± ∼ + |
| D-Glucose | ++ | Raffinose | + |
| D-Fructose | + | D-Mannitol | ± |
| Sucrose | ++ | Control(not added) | − |

(Note) In the table,
−: not assimilated;
±: doubtful assimilation;
+:assimilated;
++: well assimilated.

(2) *Streptomyces albogriseolus* No. 1953

(I) Morphorogical characteristics

The spore-bearing hyphae were simply branched from vegetative mycelia and spores occured in chains of more than 10. The form of spore-bearing aerial hyphae were spiral, open loops, sometimes flexibilis and hook. Whorls were not observed. Spores were ellipsoidal to cylindrical, 0.5 to 0.8×1.0 to 1.7μ. The surface of spores were warty or spiny [sucrose-nitrate agar, starch-inorganic salt (ISP-4), tyrosine agar (ISP-7)] and occasionally smooth [glycerin-asparagine agar (ISP-5)].

(II) Cultural characteristics

Table 4 shows the cultural characteristics of this strain, the color codes used being as mentioned hereinbefore.

TABLE 4

Cultural characteristics on *Streptomyces albogriseolus* No. 1953 on Various Media

| No. | Medium | Growth | Aerial mycelium | Reverse | Soluble pigments |
|---|---|---|---|---|---|
| 1 | Sucrose-nitrate agar | Moderate, colorless-ivory (2 ca) | Moderate, powdery, white-gray (Near grays, 2cb, 1fe) | Colorless-gray with a yellow tinge | None |
| 2 | Glucose-asparagine agar | Moderate, light yellowish brown (2ca-2ea) | Poor, white | Light yellowish brown (2ca-2ea) | None |
| 3 | Glycerin-asparagine agar (ISP 5) | Moderate, light brown with a grayish tinge (3gc, Light Tan-3ie) | Moderate, powdery, white-gray (2ca, near grays, 2cb, 1dc) | Amber (3ec, Bisque-31g, Adobe Brown) | Pale brown |

TABLE 4-continued
Cultural characteristics on *Streptomyces albogriseolus* No. 1953 on Various Media

| No. | Medium | Growth | Aerial mycelium | Reverse | Soluble pigments |
|-----|--------|--------|-----------------|---------|------------------|
| 4 | Starch-inorganic salt agar (ISP 4) | Moderate, slightly raised, colorless-ivory (2ca) | Moderate, powdery, white-gray (near grays, 2cb, Ivory Tint-2fe, Covert Gray) | Light yellowish brown (2ea)-gray (2cb, 2fe) | None |
| 5 | Tyrosine agar (ISP 7) | Moderate, ivory (2ca)-light yellowish brown (2ea) | Moderate, powdery, gray (near grays, 2cb, 2dc, 2fe), with white patches | Light yellowish brown with a gray tinge (2ie, Light Mustard Tan, 2gc, Bamboo, 2 ge, Covert Tan) | Pale brown |
| 6 | Nutrient agar | Moderate, ivory light yellowish brown (2ea) | Very sparse, white | Colorless-ivory | None |
| 7 | Yeast-malt agar (ISP 2) | Moderate, creased, with clevices. Ivory-light yellowish brown | Very sparse, white | Light yellowish brown | Pale yellowish brown |
| 8 | Oatmeal agar (ISP 3) | Moderate, thin growth, colorless-light yellowish brown | Very sparse, powdery, white | Colorless-light yellowish brown | Pale yellowish brown |

(III) Physiological characters (a) Temperature range for growth

Growth of the strain was observed in the same manner as described hereinbefore. As shown in Table 5, the optimal temperature range for growth is 28° to 40° C.

TABLE 5

| Growth temperature (°C.) | Degree of growth | Growth temperature (°C.) | Degree of growth |
|---|---|---|---|
| 15 | + | 32 | +++ |
| 20 | ++ | 37 | +++ |
| 24 | ++ | 40 | +++ |
| 28 | +++ | 45 | ++ |
| 30 | +++ | 55 | − |

(Note) In the table,
−: no growth;
+: growth;
++: good growth;
+++: luxuriant growth.

(b) Liquefaction of gelatin (glucose-peptone gelatin, 28° C.): positive;

(c) Hydrolysis of starch (starch-inorganic salt agar, 28° C.): positive;

(d) Coagulation and peptonization of skim milk (skim milk, 37° C.): positive but weak coagulation, positive peptonization;

(e) Reduction of nitrates (peptone water with 1% potassium nitrate, 28° C., 3 weeks): negative;

(f) Production of melanoid pigments:

Tyrosine agar: pale brown pigment

Peptone-yeast extract-iron agar: negative Tryptone-yeast broth: negative (IV) Assimilation of carbon sources (Pridham-Gottlieb agar):

The carbohydrate assimilation spectrum of this strain is presented in Table 6.

TABLE 6

| Carbon source | Degree of assimilation | Carbon source | Degree of assimilation |
|---|---|---|---|
| L-Arabinose | + | i-Inositol | ++ |

TABLE 6-continued

| Carbon source | Degree of assimilation | Carbon source | Degree of assimilation |
|---|---|---|---|
| D-Xylose | + | L-Rhamnose | ++ |
| D-Glucose | ++ | Raffinose | + |
| D-Fructose | + | D-Mannitol | + ~ ++ |
| Sucrose | + | Control (not added) | − |

(Note) In the table,
−: not assimilated;
+: assimilated;
++: well assimilated.

It should of course be understood that any other strain of the genus Streptomyces which is able to produce P-1894B, inclusive of artificial mutants thereof, may likewise be employed for the purposes of this invention.

Cultivation of the P-1894B-producer may be carried out using a fluid medium or a solid medium, although it is normally advantageous to grow the strain in a fluid medium under shaking or aerobic stirred conditions.

The culture medium may be of any type only if it leads itself well to growth of Streptomyces and permits extracellular production of P-1894B. Thus, the medium may contain, as carbon sources, glucose, lactose, glycerin, starch, sucrose, dextrin, molasses, organic acids (e.g. acetic acid, tartaric acid, etc.) and so on. As examples of the nitrogen sources which may be present in the medium, there may be mentioned peptone, Casamino acid (Difco), N-Z Amine A (Sheffield) and other protein hydrolysates, yeast extract, malt extract, soybean cake, corn steep liquor, amino acids (e.g. aspartic acid, glutamic acid, etc. various ammonium salts (e.g. ammonium sulfate, ammonium chloride, etc.) and so on. As inorganic salts, various phosphates (e.g. monosodium phosphate, dipotassium phosphate, etc.), metal salts such as magnesium sulfate, sodium chloride, ferrous sulfate, heavy metal salts (such as manganese sulfate, zinc sulfate, etc.) and so on may be incorporated in the medium. Also, for the purpose of promoting growth of the strain, there may also be added vitamins (e.g. vitamin B₁, calcium pantothenate, etc.), nucleic acid related compounds (e.g. adenine, uracil, etc.) and so on.

Depending on the cultural method and conditions, it may be in certain cases advantageous to add an antifoam such as silicone oil, polypropylene glycol derivatives (e.g. Actocol, Takeda Chemical Industries, Ltd.), soybean oil, etc., all of which may lead to an increased production of P-1894B.

While the temperature and time of cultivation, pH of the medium and other cultural conditions depend on the particular strain, composition of medium and other factors, the cultural conditions may be suitably selected so that the yield of P-1894B will be maximal. Thus, in many instances, it is advantageous to incubate the strain at about 20° to 40° C. under aerobic conditions for one to 10 days, the pH of the medium being maintained at about 4 to 9.

Various procedures may be advantageously followed in a suitable combination to isolate the antifibrotic substance P-1894B from the culture broth thus produced. Thus, such procedures include extraction with a water-immiscible organic solvent under neutral or weakly acidic conditions, said solvent being for example ethyl acetate, butyl acetate, chloroform, butanol, benzene, toluene, diethyl ether, methylene chloride or methyl isobutyl ketone; adsorption chromatography with activated carbon, silica gel, alumina or the like; gel filtration on a Sephadex column; and ion-exchange chromatography on an ion exchange resin. By means of a suitable combination of such procedures is it possible to isolate from the broth the desired antifibrotic substance P-1894B as crystals or crystalline powders.

The properties of thus-obtained antifibrotic substance P-1894B are as follows.

(1) Physical and chemical properties (a) Melting point: 165°-172° C.;

(b) Elementary analysis: C, 62.62±1.0; H, 6.28±0.5; O, 30.06±0.

P-1894B consists of C, H and O, with no evidence of N. (as determined with Perkin-Elmer Model 240)

(c) Molecular weight: about 1000 (by vapor pressure osmometry with ethyl acetate as the solvent)

(d) Specific rotation: $[\alpha]_D^{25} = +155° \pm 15°(c=0.419,$ methanol)

(e) Color reactions:
  (i) Naphthoresorcinol-sulfuric acid: positive reaction (greenish black)
  (ii) Alcoholic magnesium acetate: positive reaction (bluish violet)
  (iii) Ninhydrin: negative reaction.
  (iv) Barton's reagent: negative reaction (f) Solubility: Readily soluble or soluble in chloroform, dioxane, ethyl acetate, dimethylsulfoxide, acetone, methyl ethyl ketone, pyridine, methanol, ethanol, benzene, toluene, diethyl ether and 0.1 N NaOH; sparingly soluble or insoluble in petroleum ether, n-hexane and cyclohexane.

Figure 1:
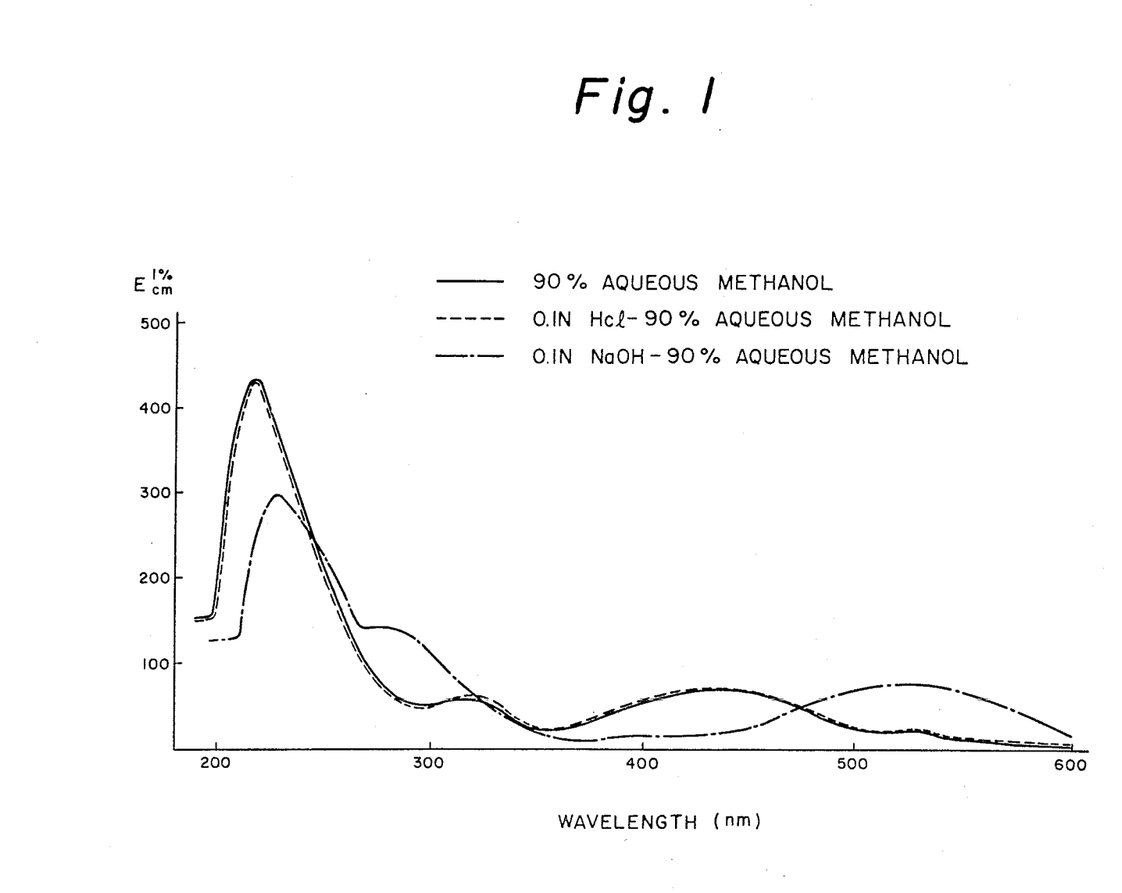

(g) Absorptions in the untraviolet and visible region of the spectrum:
FIG. 1 shows the absorptions of antifibrotic substance P-1894B in the ultraviolet and visible region of the spectrum.

In the diagram, the solid line represents the spectrum as measured in 90% aqueous methanol; the dotted line the spectrum in 0.1 N HCl-90% aqueous methanol; and the broken line in 0.1 N NaOH-90% aqueous methanol. The wavelengths (nm) and $E_{1\,cm}^{1\%}$ giving absorption maxima immediately after dissolution in various solvents are presented below.

| Solvent | Wavelength ($E_{1cm}^{1\%}$) |
|---|---|
| 90% aqueous methanol: | 218 ± 2(432 ± 40), 318 ± 2(59 ± 6), 440 ± 2(71± 7) |
| 0.1N HCl-90% aqueous methanol: | 218 ± 2(427 ± 40), 318 ± 2(62 ± 6), 435 ± 2(70 ± 7) |
| 0.1N NaOH-90% aqueous methanol: | 228 ± 2(297 ± 30), 282 ± 2(144 ± 14), 530 ± 2(77 ± 8) |

Figure 2:
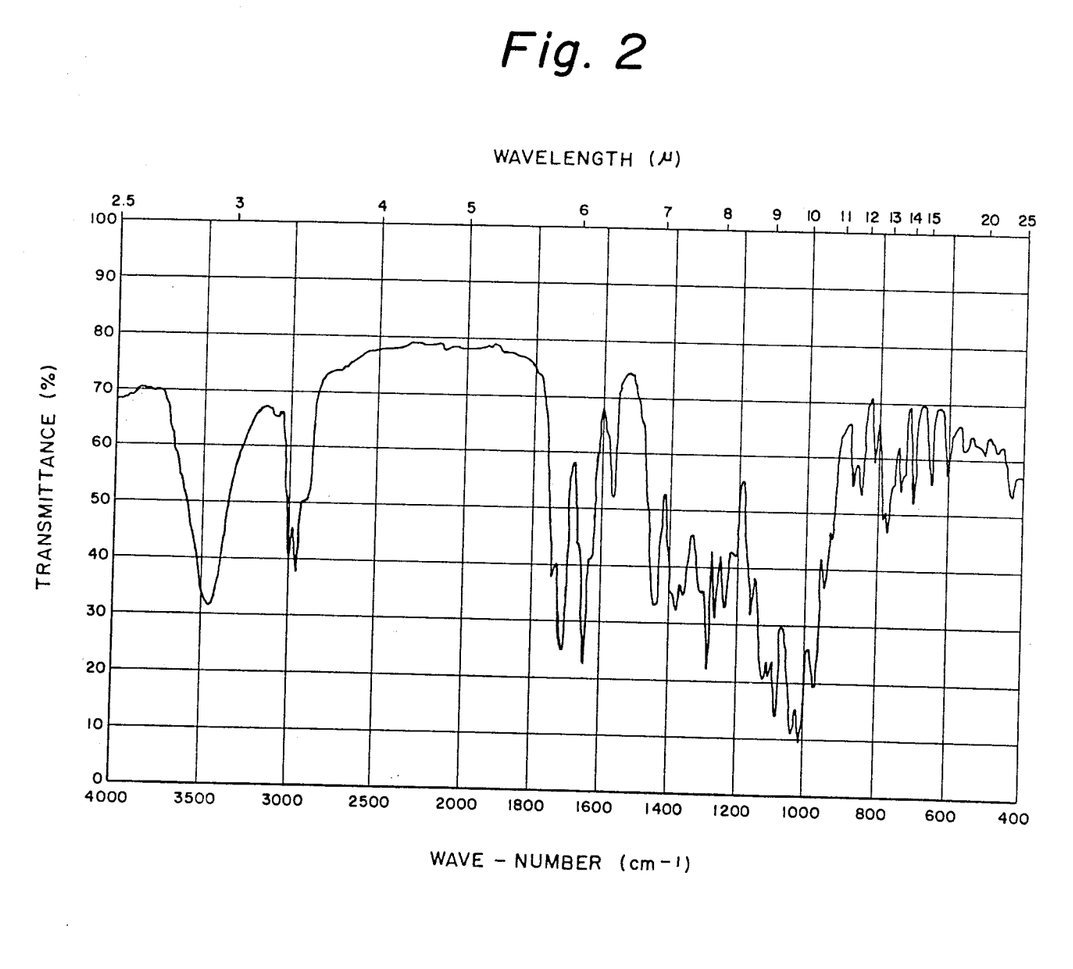

(h) Infrared absorption spectrum: FIG. 2 shows the absorptions of P-1894B in the infrared region of the spectrum (KBr). The main wave-numbers giving absorption maxima are as follows.
3430, 2980, 2950, 1740, 1705, 1645, 1570, 1440, 1380, 1290, 1120, 1100, 1080, 1040, 1010, 970 cm$^{-1}$ (i) General property and appearance:
weakly acidic; crystals orange-yellow to orange-red.

(j) PKa: 10.15 (by titrimetry, in 66.7% aqueous DMF)

Figure 3:
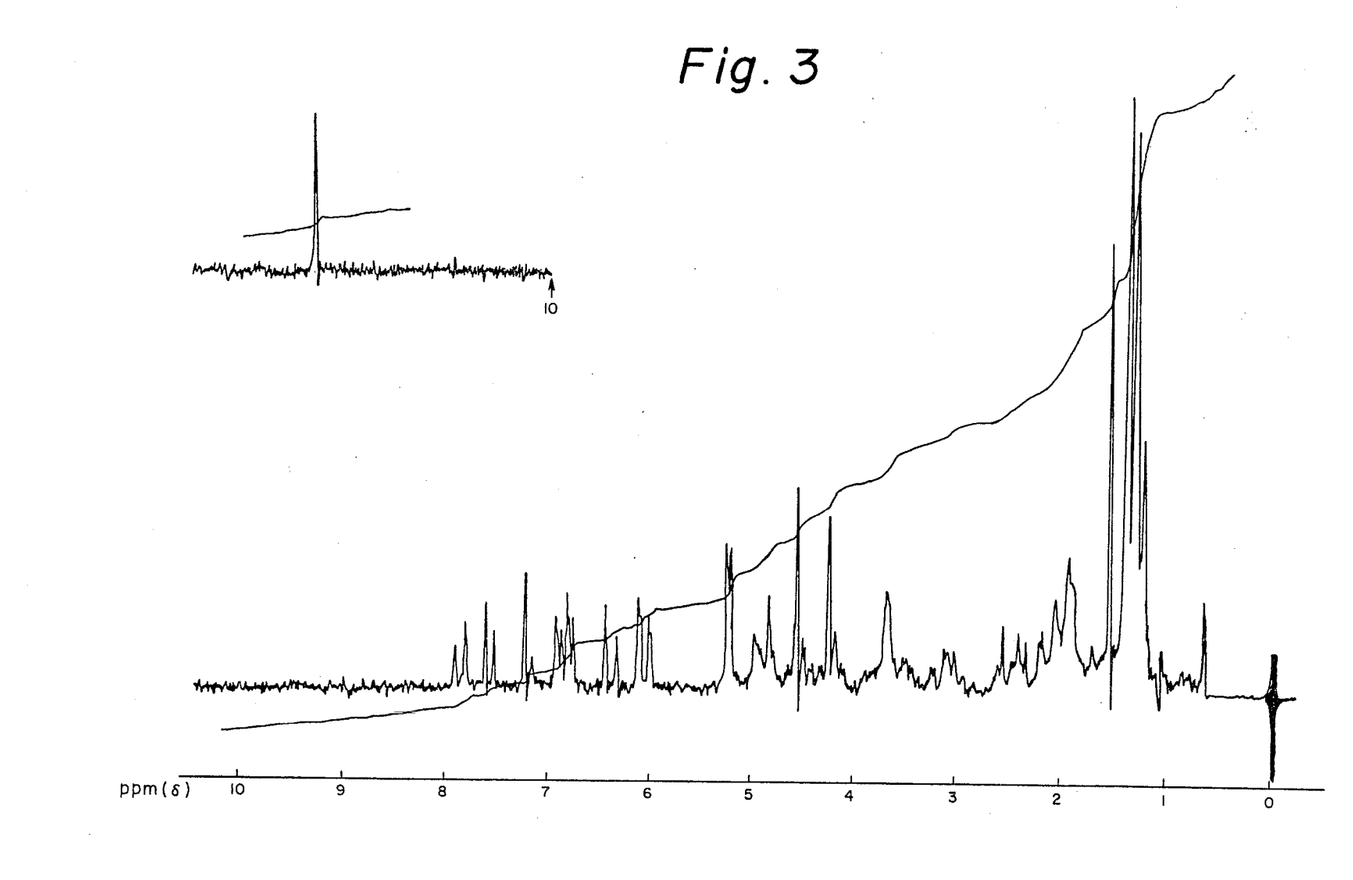

(k) NMR: The NMR spectrum determined in deuteriochloroform at 90 MHz is shown in FIG. 3.

(k) TLC Rf: The Rf values on the silica gel plate (Merck, Product No. 5715) are as follows.

| Solvent | Rf |
|---|---|
| Water | 0 |
| Chloroform | 0.01 |
| Chloroform-acetone (10:1) | 0.21 |
| Chloroform-ethyl acetate (2:3) | 0.50 |
| Chloroform-ethylacetate (1:1) | 0.32 |
| H₂O-saturated butyl acetate | 0.40 |
| Acetone-n-hexane (1:1) | 0.70 |
| Benzene-methanol (10:1) | 0.56 |
| n-Butanol-acetic acid-H₂O(3:1:1) | 0.80 |
| Ethyl acetate | 0.83 |
| Chloroform-methanol (10:1) | 0.96 |
| Acetone | 0.97 |

Comparison of P-1894B having the above-mentioned physical and chemical properties with the known described substances shows that P-1894B resembles Aquayamycin, Ayamycin A₂, TA-435A and Julymycin B-II. However, P-1894B is different from: Aquayamycin in melting point, molecular weight and TLC behavior (Rf) [J. Antibiotics 21, No. 2, 91–97 (1968)], Ayamycin A₂ in melting point and specific rotation [J. Antibiotics, Ser A, 13, No. 5, 321–326 (1960)], TA-435A in TLC behavior (Rf) [J. Antibiotics 21, No. 2, 91–97 (1968)] and Julymycin B-II in molecular weight, specific rotation, UV spectrum and TLC behavior (Rf) [J. Antibiotics, Ser A, 17, No. 4, 156–160 (1964) and J. Antibiotics 21, No. 2, 91–97 (1968)]. It is thus considered that the antifibrotic substance P-1894B is a new substance.

(2) Biological properties (I) Protocollagen proline hydroxylase inhibitor activity: The inhibitory activity assay was carried out by the method of R. E. Rhoads et al [Methods in Enzymology XVIIB, 306 (1979)] using a partially purified enzyme preparation obtained from chick embryos in accordance with the methods of K. I. Kivirriko et al and J. Halme et al (J. Biol. Chem. 242, 4007 (1967) and Biochim. Biophys. Acta 198, 460 (1967) and, as the substrate, (Pro-Pro-Gly)₅.4H₂O [prepared by Tanpakushitsu Kenkyū Shōrei Kai (Protein Research Foundation), Osaka]. The assay showed that the concentration of P-1894B required for a 50% inhibition of 100 μg (as protein) of said partially purified enzyme was about 7 μg/ml.

(II) Collagen biosynthesis inhibiting activity:

Basically in accordance with a procedure described by R. A. Salvador et al [Arch. Biochem. Biophys. 174, 382 (1976)], 0.3 mg/kg was intraperitoneally administered to Sprague-Dawley rats (female, 3 weeks old) once daily for 6 days and the amounts of collagen and non-collagenous proteins in the uteri were compared with the figures for control. As will be seen from Table 7, P-1894B inhibited the biosynthesis of collagen specifically and significantly.

| Group | weight(g) initial | weight(g) final | Protocollagen proline hydroxylase (dpm*/mg of protein) | Hydroxyproline (μg/100 mg of protein) |
|---|---|---|---|---|
| Saline (control) | 113 ± 5 | 210 ± 13 | 263 ± 70 | 79.4 ± 8.5 |
| CCl₄ | 111 ± 5 | 193 ± 8 | 504 ± 87 | 145.8 ± 18.3 |
| CCl₄ + P-1894B 3.25mg/kg/day | 112 ± 9 | 199 ± 19 | 457 ± 68 | 132.4 ± 29.6 |
| 6.16mg/kg/day | 111 ± 5 | 198 ± 9 | 357 ± 15** | 122.6 ± 14.0** |

*decay per minute
**Significantly different from CCl₄ group, $P<0.05$, n=5.

TABLE 7

| Group | Body weight of rats (g) | Total protein of uterus (mg) | Collagen in uterus (mg) | Non-collagenous protein[a] in uterus (mg) | % Inhibition[b] Collagen | % Inhibition[b] Non-collagenous protein |
|---|---|---|---|---|---|---|
| (A) Control (1) | 86 ± 4 | 13.9 ± 1.6 | 3.12 ± 0.48 | 10.78 ± 1.14 | — | — |
| (B) Control (2) 17β-estradiol (5 μg) | 82 ± 4 | 28.6 ± 7.3 | 4.39 ± 0.16 | 24.21 ± 7.21 | — | — |
| (C) 17β-estradiol (5 μg) + P-1894B(0.3 mg/kg) | 72 ± 5 | 30.4 ± 5.0 | 3.41 ± 0.22 ($p < 0.01$)[c] | 26.99 ± 4.67 | 78 | −21 |

[a]Non-collagenous protein = total protein − collagen.
[b]Percent inhibition = $\frac{(B) - (C)}{(B) - (A)} \times 100$
[c]Significantly different from the value of control (2).
The experiment was performed in groups of 4 rats.

(III) Effect of P-1894B on collagen biosynthesis in carbon tetrachloride-induced hepatic cirrhosis:

Female Sprangue-Dawley rats weighing approximately 110 g each were divided into 4 groups. Group I (control) received saline (1 ml/rat) and Groups II, III and IV received 10% CCl₄-olive oil mixture (1 ml/rat) intraperitoneally twice weekly for a total 8 doses. Groups III and IV received P-1894B orally with food for 4 weeks. Average doses of P-1894B in Groups III and IV were 3.25 and 6.16 mg/kg/day, respectively. The rats were sacrificed a day after the last injection and the livers were immediately removed for the assays.

Assay of protocollagen proline hydroxylase activity:

A 10% homogenate of the liver was prepared in 20 mM Tris-HCl buffer, pH 7.5, containing 0.2 M NaCl, 0.1 M glycine, $5\times10^{-5}$ M 1,4-dithiothreitol and 0.1% Triton (polyethylene glycol p-isooctylphenyl ether) X-100 using a Polytron homogenizer. The homogenate was centrifuged at 15,000 g for 20 min and the clear supernatant was assayed for proline hydroxylase activity by the method of Hutton et al [Anal. Biochem. 16, 384–394 (1966)]. The protein content of the homogenate was measured by the method of Lowry et al [J. Biol. Chem. 193, 265–275 (1951)] using bovine serum albumin as the standard.

Assay of hydroxyproline content:

Hydroxyproline content of the liver was measured in 6 N HCl hydrolysate (110° C., 22h) by the method of Blumenkrantz et al [Anal. Biochem. 63, 331–340 (1975)].

Table 8 shows that on treatment with P-1894B (6.16 mg/kg/day, p.o.), the specific activity of protocollagen proline hydroxylase and hydroxyproline content in the liver was significantly decreased as compared to livers of CCl₄-fibrotic rats that had not received P-1894B.

(IV) Acute toxicity: $LD_{50}$, 50~100 mg/kg (mouse, intraperitoneal)

As mentioned hereinbefore, P-1894B is a novel substance having protocollagen proline hydroxylase inhibitor and selective collagen biosynthesis inhibitor activities, and is, therefore, of value for example as a biochemical reagent or an inhibitor of animal tissue fibrosis.

As an inhibitor of animal tissue fibrosis, P-1894B can be used in the prophylaxis and treatment of organ fibrosis in animals, particularly in mammalian animals (laboratory animals such as rabbit, rat and mouse; pet animals such as dog and cat; and human being). Organ fibrosis is a generic term denoting the various diseases arising from an excess deposit of collagen, and covers such diseases as pulmonary fibrosis, hepatic cirrhosis, nephtosclerosis, arteriosclerosis, scleroderma, myelofibrosis, chronic arthritis, etc. [Hotchi: Naika (Internal Medicine) 41, 724 (1978)].

For use in the prophylaxis or treatment of organ fibrosis, P-1894B can be orally or otherwise administered, either as it is or in combination with an appropriate pharmacologically acceptable carrier, excipient or diluent, in such dosage forms as powders, granules, tablets, capsules and injections. The dosage depends on the target disease, condition, subject, administration route and other factors. For the prophylaxis or treatment of hepatic cirrhosis, arteriosclerosis or chronic arthritis in an adult human being, for instance, the substance is desirably administered by the oral route at a daily dose level of about 2 to 50 mg in a single dose or up to 3 divided portions.

The following working examples are intended merely to illustrate presently preferred embodiments of the present invention and not to restrict the scope of this invention.

EXAMPLE 1

*Streptomyces albogriseolus* subsp. No. 1894 (ATCC 31422; IFO 13881) was used to inoculate two 2-liter Sakaguchi flasks each containing 500 ml of a fluid medium (pH 7.0) composed of 2.0% glucose, 1.0% glycerin, 0.5% raw soybean flour, 0.5% corn steep liquor, 0.3% polypeptone, 0.3% sodium chloride and 0.5% calcium carbonate, and the inoculated flasks were incubated and a reciprocal shaker at 28° C. for 3 days to obtain about 1 liter of culture. This culture was transferred to a 50 l-fermenter containing 30 l of the same medium as above and incubated at 28° C. for 3 days, with aeration and stirring. The resulting culture, 15 l, was further transferred to a 200-l fermenter containing 100 l of a fluid medium (pH 7.0) composed of 5% dextrin, 3% raw soybean flour, 0.7% polypeptone, 0.5% ferrous sulfate, 0.05% magnesium sulfate, 0.05% manganese sulfate, 0.05% dipotassium phosphate and 0.5% calcium carbonate. The medium was thus incubated at 28° C. for 2 days, with aeration and stirring. To about 80 l of the resultant broth was added 2 kg of Topco perlite #34 (Toko Perlite Kogyo K.K.) and the mixture was filtered by means of a filter press coated with 6 kg of Hyflo Super-Cel (Johne-Manville) to obtain about 70 l of filtrate. The filtrate was adjusted to pH 3.0 with sulfuric acid and extracted twice with 25 l of ethyl acetate. The extracts were combined and washed twice with 15 l of water. The washed extract was concentrated under reduced pressure to recover about 150 ml of concentrate. This concentrate was diluted by addition of about 50 ml of chloroform and passed through a column (4×32 cm) of silicic acid (Merck), elution being carried out with 2 l of chloroform. The P-1894B fractions were pooled and concentrated under reduced pressure, followed by addition of 500 ml of n-hexane to about 50 ml of concentrate, whereupon the active substance was precipitated as oil. The oily fraction was dissolved in a small amount of ethyl acetate and passed through a column (4×40 cm) of silicic acid treated with n-hexane. The fraction emerging with 2 l of n-hexane-chloroform (1:1) was discarded and the P-1894B fraction was eluted out with chloroform-ethyl acetate (1:1) and concentrated to dryness under reduced pressure. The dry concentrate was dissolved in a small amount of chloroform and passed through a column (3.5×31 cm) of silicic acid pretreated with chloroform. The fraction emerging with 1.2 l of chloroform was discarded. The P-1894B fractions eluted out with chloroform-ethyl acetate (1:1) were pooled (about 600 ml) and concentrated under reduced pressure. To 50 ml of concentrate was added 300 ml of n-hexane, whereupon about 1.15 g crude powders of P-1894B were precipitated. These crude powders were dissolved in chloroform-toluene (1:1), concentrated under reduced pressure and cooled. By the above procedure were obtained about 920 mg of yellow-orange crude crystals. The crude crystals were further recrystallized from diethyl ether solution to recover about 660 mg of P-1894B as orange-yellow crystals.

EXAMPLE 2

*Streptomyces albogriseolus* subsp. No. 1894 (ATCC 31422; IFO 13881) was cultivated in exactly the same manner as Example 1 and about 80 l of the resulting culture broth was centrifuged in a Sharples (Sharples corporation, U.S.A.) centrifuge to remove the cells and other solid matter. About 70 l (pH 8.3) of the resultant supernatant was extracted twice with 25 l each of ethyl acetate and the extracts were pooled and washed twice with 10 l of aqueous hydrochloric acid (pH 3.0) and twice with 15 l of water. The washed extract was concentrated under reduced pressure and 500 ml of n-hexane was added to 80 ml of concentrate, whereupon the active substance was precipitated as oil. This precipitate was recovered, dissolved in a small amount of chloroform and passed through a column (3.5×31 cm) of silicic acid pretreated with chloroform. The fraction emerging with 1 l of chloroform was discarded and the column was further eluted with chloroform-ethyl acetate (1:1). The P-1894B fractions were pooled (500 ml), concentrated under reduced pressure and rechromatographed in the same manner as above. The active fractions were pooled to recover 300 mg of dry powders. The powders were recrystallized as in Example 1 to obtain 80 mg of P-1894B as orange-yellow crystals.

EXAMPLE 3

*Streptomyces albogriseolus* No. 1953 (ATCC 31423, IFO 13882) was used to inoculate two 2-l Sakaguchi flasks each containing 300 ml of a fluid medium (pH 7.0) composed of 2% glucose, 1% glycerin, 0.5% raw soybean flour, 0.5% corn steep liquor, 0.3% polypeptone, 0.3% sodium chloride and 0.5% calcium carbonate, and each inoculated flask was incubated on a reciprocating shaker at 28° C. for 3 days to obtain 1 l of culture. This culture was transferred to a 50-l fermenter containing 30 l of a fluid medium (pH 7.2) composed of 5% dextri, 3% raw soybean flour, 0.5% polypeptone, 0.001% ferrous sulfate, 0.05% magnesium sulfate, 0.001% manganese sulfate, 0.05% dipotassium phosphate and 0.5% calcium carbonate and aeration-agitation culture was carried out at 28° C. for 3 days. About 26 l of the resultant culture broth was filtered with a filter press and the filtrate was adjusted to pH 3.0 with hydrochloric acid and extracted twice with 10 l each of ethyl acetate. The extracts were combined and washed with 10 l of water. The washed extract was concentrated under reduced pressure and 50 ml of the concentrate was passed through a column (3×43 cm) of 130 g silicic acid, elution being carried out with ethyl acetate. The active eluate, 750 ml, was concentrated under reduced pressure and 30 ml of concentrate was passed through a column (3×36 cm) of 110 g silicic acid. The impurity-containing fraction emerging with 400 ml of chloroform was discarded and, then, the active compound was eluted with chloroform-ethyl acetate (4:1). The active fractions were pooled and concentrated to dryness. The concentrate was dissolved in a small amount of chloroform and re-chromatographed in the same manner as the second chromatography. The active fractions thus obtained were combined, concentrated and precipitated with n-hexane to obtain about 210 mg of crude powders, which were then recrystallized from toluene. By the above procedure was obtained 100 mg of P-1894B as orange-red crystals.

EXAMPLE 4

Some typical formulations of P-1894B for the prophylaxis and treatment of organ fibrosis are as follows.

A. Tablets

Five (5) milligrams of P-1894B, 47 mg of lactose, 40 mg of corn starch, 12 mg of hydroxypropyl-cellulose-L and 1 mg of magnesium stearate are admixed together and the mixture is tableted in accordance with the established pharmaceutical procedure (wet-granulation method).

B. Capsules

| | |
|---|---|
| (1) P-1894B | 5 mg |
| (2) Lactose | 130 mg |
| (3) Corn starch | 60 mg |
| (4) Magnesium stearate | 5 mg |
| Total (per capsule) | 200 mg |

The indicated amounts of (1), (2), (3) and one-half of the indicated amount of (4) are admixed together and granulated. Then, the remainder of (4) is added to the granules and the entire composition is sealed into a No. 2 gelatin capsule (Japanese Pharmacopeia 9th Ed.).

What we claim is:

1. Antifibrotic substance P-1894B which has the following physical and chemical properties:
   (a) Melting point: 165°–172° C.
   (b) Elementary analysis: C, 62.62±1.0; H, 6.28±0.5; O, 30.06±1.0;
   (c) Molecular weight: about 1000 (as determined by vapor pressure osmometry with ethyl acetate as the solvent);
   (d) Specific rotation: $[\alpha]_D^{25} = +155° \pm 155°$ (c=0.419, methanol);
   (e) Color reactions: positive naphthoresorcinol-sulfuric acid and alcoholic magnesium acetate reactions; negative ninhydrin and Barton's reactions;
   (f) Solubility: readily soluble or soluble in chloroform, dioxane, ethyl acetate, dimethylsulfoxide, acetone, methyl ethyl ketone, pyridine, methanol, ethanol, benzene, toluene diethyl ether and 0.1 N NaOH; sparingly soluble or insoluble in water, 0.1 N HCl, petroleum ether, n-hexane and cyclohexane;
   (g) Absorptions in the ultraviolet and visible region of the spectrum: the wavelengths (nm) giving absorption maxima immediately after dissolution in the following solvents:

| Solvent | Wavelengths |
|---|---|
| 90% aqueous methanol: | 218 ± 2, 318 ± 2, 440 ± 2 |
| 0.1N HCl-90% aqueous methanol: | 218 ± 2, 318 ± 2, 435 ± 2 |
| 0.1N NaOH-90% aqueous methanol: | 228 ± 2, 282 ± 2, 530 ± 2 |

(h) Absorptions in the infrared region of the spectrum: the main wavenumbers giving absorption maxima as determined by the potassium bromide method:
   3430, 2980, 2950, 1740, 1705, 1645, 1570, 1440, 1380, 1290, 1120, 1100, 1080, 1040, 1010, 970 cm$^{-1}$
   (i) General property and appearance: weakly acidic; crystals orange-yellow to orange-red.

2. A pharmaceutical composition for the prophylaxis or treatment of fibrosis due to excessive collagen accumulation in a mammalian animal, which contains an effective amount of the anti-fibrotic substance P-1894B as defined in claim 1 for the prophylaxis or treatment of said fibrosis and a pharmaceutically acceptable carrier.

3. A composition according to claim 2, which is in the form of a powder, granulate, tablet, capsule or injection.

4. A method for the prophylaxis or treatment of fibrosis due to excessive collagen accumulation in mammalian animals which comprises administering the antifibrotic substance P-1894B as defined in claim 1 in a daily amount of from about 2 mg to 50 mg per dosage unit.

5. A method according to claim 4, wherein the fibrosis is hepatic cirrhosis.

6. A process for producing an antifibrotic substance P-1894B as defined in claim 1, which comprises culturing a P-1894B-producing microorganism selected from the group consisting of *Streptomyces albogriseolus* subsp. No. 1894 (ATCC 31422) and *Streptomyces albogriseolus* No. 1953 (ATCC 31423) in a culture medium containing an assimilable carbon source and a digestible nitrogen source under aerobic conditions at a pH of from about 4 to about 9 and at a temperature of from about 20° to about 40° C. until the P-1894B has accumulated in the culture medium, and recovering the P-1894B therefrom.

* * * * *

Disclaimer 4,260,599.—*Hisayoshi Okazaki*, Kyoto; *Tsuneo Kanamaru*, Takatsuki, and Kazuhiko Ohta, Ikeda, Japan. ANTIFIBROTIC SUBSTANCE P-1894B. Patent dated Apr. 7. 1981. Disclaimer filed July 1, 1982, by the assignee, *Takeda Chemical Industries, Ltd.*

Hereby enters this disclaimer to claim 1 of said patent.

[*Official Gazette September 21, 1982.*] -